Figure 1:
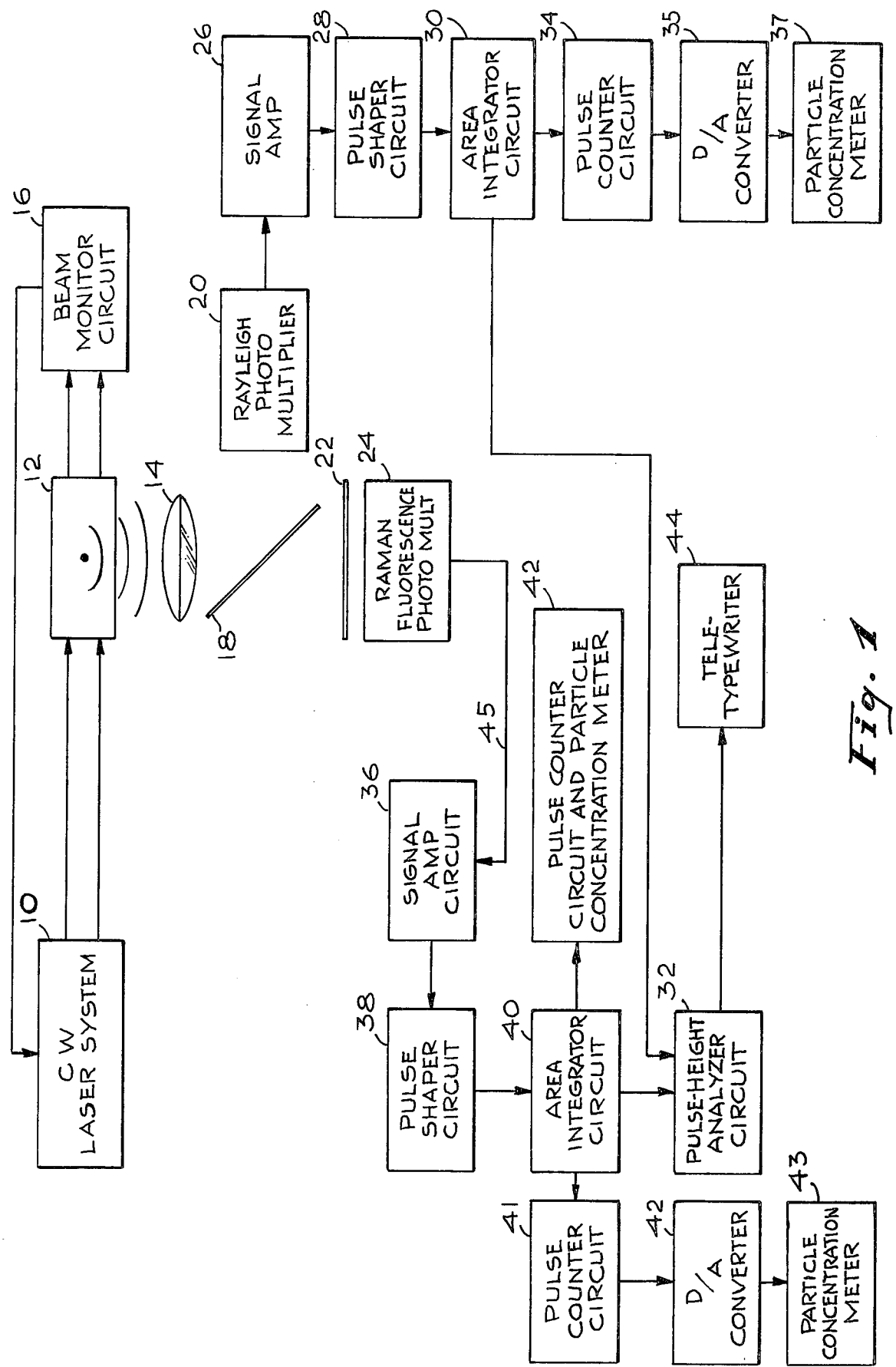

United States Patent [19]

Falconer

[11] 4,071,298
[45] Jan. 31, 1978

[54] LASER RAMAN/FLUORESCENT DEVICE FOR ANALYZING AIRBORNE PARTICLES

[75] Inventor: David G. Falconer, Menlo Park, Calif.

[73] Assignee: Stanford Research Institute, Menlo Park, Calif.

[21] Appl. No.: 686,942

[22] Filed: May 17, 1976

Related U.S. Application Data

[63] Continuation-in-part of Ser. No. 483,786, June 27, 1974, abandoned.

[51] Int. Cl.$^2$ .............................. G01N 15/02
[52] U.S. Cl. ........................ 356/73; 356/75; 356/85; 356/102; 356/103
[58] Field of Search .................. 356/73, 75, 85, 102, 356/103, 104

[56] References Cited

U.S. PATENT DOCUMENTS

| | | | |
|---|---|---|---|
| 3,710,933 | 1/1973 | Fulwyler et al. | 356/75 |
| 3,817,622 | 6/1974 | Billman et al. | 356/73 |
| 3,850,525 | 11/1974 | Kaye | 356/75 |

Primary Examiner—Vincent P. McGraw
Attorney, Agent, or Firm—Lindenberg, Freilich, Wasserman, Rosen & Fernandez

[57] ABSTRACT

A laser Raman/fluorescent electro-optical device is described for counting, sizing, weighing and assaying airborne particles, whereby the physical state of the atmosphere may be monitored.

7 Claims, 2 Drawing Figures

LASER RAMAN/FLUORESCENT DEVICE FOR ANALYZING AIRBORNE PARTICLES

CROSS REFERENCE TO RELATED APPLICATIONS

This application is a continuation-in-part of application Ser. No. 483,786 filed June 27, 1974, now abandoned.

BACKGROUND OF THE INVENTION

This invention relates to optical devices for monitoring the physical and chemical state of the atmosphere, and more particularly to improvements therein.

Optical scattering techniques provide a particularly attractive method for monitoring the physcial and chemical state of the atmosphere. Such methods have a natural simplicity and lead to reliable and economical hardware configurations. Rayleigh lidar techniques, for example, provide an excellent means for detecting cloud and smog layers, locating temperature inversions and aerosol layers, and determining cloud structure through rain and fog cover. Raman lidar instruments, on the other hand, offer a tool for selectively detecting and measuring atmospheric pollutants, such as carbon monoxide, sulphur dioxide, and oxides of nitrogen. Finally, Rayleigh light-scattering particle counters provide a convenient technique for detecting and sizing individual aerosol particles.

RAYLEIGH-SCATTERING TECHNIQUES

Rayleigh particle counters measure a wide range of particle sizes (0.3 microns and larger), operate at high counting rates (on the order of 1000 particles per second), and offer good sizing accuracy ($\pm$ 30 percent for tungsten sources and $\pm$ 3 percent for laser sources). These devices operate by passing aerosol particles through a collimated laser beam or a focused tungsten source. Light scattered by an aerosol particle is collected by a mirror or lens and then relayed to the photocathode of a photo-multiplier tube. The photomultiplier current pulses are then amplified, shaped, counted, and histogrammed by appropriate electronic circuitry. The number of counts registered per second indicates the particle concentration, and the histogram provides a size-frequency distribution for the detected particles.

The chief drawbacks of the conventional light-scattering particle counter are its inability to measure particle mass and its inability to determine particle chemistry. To ascertain the mass and chemistry of an aerosol particle, one must measure the differential—rather than the total—Rayleigh-scattering cross section. Additionally, the differential cross section must be measured at several critical wavelengths, that is, wavelengths where the suspected chemical components have strong absorption bands. Using these measurements and their assigned errors, one can attempt to separate the scattering effects caused by the shape of the particle from the scattering effects caused by its complex refractive index. By studying the behavior of the complex refractive index as a function of wavelength, one can estimate the particle mass and speculate on its chemical composition.

The above procedure—though workable in theory—gives rise to certain technical difficulties in practice. In particular, to attain reasonable counting rates, one must abandon the angular and wavelength scanning techniques used in commercial nephelometers. Instead, a hardware arrangement that simultaneously measures the scatteredlight intensity at several polar angles and several wavelengths must be realized. The number of angles and number of wavelengths at which samples must be taken depends on the physical and chemical makeup of the particle. (Oddly shaped particles with many chemical components require well-sampled, high-precision cross-section measurements.) Owing to the practical difficulty of building such an instrument, little hope is held for weighing and assaying aerosol particles with Rayleigh-scattered light.

OBJECTS AND SUMMARY OF THE INVENTION

An object of this invention is to provide apparatus which can weigh and assay airborne particulate matter.

Another object of this invention is the provision of novel apparatus for use in air-pollution detection and measurement.

Still another object of this invention is to provide apparatus whereby the mass and chemistry of aerosol particles may be determined.

The method used by this invention for determining the mass and chemistry of an aerosol particle is to examine the Raman spectrum of the scattered light. Raman scattering differs from Rayleigh scattering in that the molecules of the particle shift the frequency of the incident light in the Raman case but leave it unaltered in the Rayleigh case. The frequency shift results from small nonlinearities in the polarizability of the scattering molecule. The nonlinearity causes mixing of the incident-light oscillations and vibrational-rotational motion of the molecule. Accordingly, the scattered light contains upper (anti-Stokes) and lower (Stokes) sidebands about the exciting frequency. Typically, one uses visible or ultraviolet light to illuminate the target molecules and looks for sidebands displaced above and below the exciting line by infrared frequencies.

The infrared frequencies modulated onto the exciting line are highly specific to the scattering molecule and independent of the exciting frequency. These frequencies arise when the molecule makes a quantum transition between one vibrational or rotational state and another owing to the influence of a perturbing external electric field. In practice, the Stokes line appears more intense than the anti-Stokes line, since, according to the Boltzmann distribution, the excited molecular states have much smaller populations than the ground state.

Hexane, for example, has a strong C—H stretching line located 2880 cm$^{-1}$ below the exciting frequency, whereas polystyrene has a strong C=C stretching vinyl line at 1632 cm$^{-1}$ below the exciting frequency. Accordingly, one might attempt the detection of individual hexane droplets or polystyrene spheres by illuminating these particles with collimated laser light and then examining the spectrum of the Raman-scattered light. Similarly, to weigh such particles, one could measure the intensity of the Raman-scattered light and then use the tabulated scattering cross section to determine the mass of the particle.

Resonance scattering offers dramatic increases in the counter's diameter sensitivity. With the resonance technique, one illuminates the target particle with laser radiation near one of the atomic transition frequencies of, say, a carbon or nitrogen atom. Owing to the strong absorption of incident photons, the Raman scattering cross section increases as much as six orders of magnitude, so that one can size particles as much as two orders of magnitude smaller than with nonresonance techniques. Accordingly, resonance scattering might allow one to weigh and assay particles on the order of 0.1 microns. (One can use either a tuned-dye or Zeeman-split laser to secure coincidence between the laser-emission and atomic-transition frequencies.)

Fluorescent-scattered light may also be used to determine the mass and chemistry of an airborne particle. As in Raman scattering, the molecules of the target particle shift the frequency of the incident light, thereby giving rise to radiation characterizing the chemistry of the particle. The fluorescent process begins when the incident light—with or without the aid of thermal processes—boosts the illuminated molecules to a higher energy state. After a time the energized molecules begin returning to their original ground state. During return the molecules cascade from energy level to energy level by emitting thermal and visible photons. Typically, one uses visible or ultraviolet light to illuminate the target molecules and looks for fluorescent radiation at optical and infrared frequencies.

Unlike the Raman effect, the fluorescent spectrum emitted by an illuminating particle depends both on the chemistry of the target particle and the frequency of the exciting light. Accordingly, research spectroscopists commonly publish two curves when reporting fluorescent spectra. One, the excitation spectrum, specifies the fluorescent intensity at a particular wavelength as a function of the exciting frequency; the other, the emission spectrum, gives the fluorescent intensity as a function of the emission wavelength for a particular exciting frequency. Accordingly, the fluorescent technique features an extra degree of freedom when compared with Raman spectroscopy. That is, the fluorescent spectroscopist can select both an exciting frequency and emission wavelength to optimize his sensitivity to a given chemical component of the target particle.

Fluorescent spectroscopy also features extremely high sensitivities, often 10 - 1000 times more sensitive than comparable absorption-spectroscopy techniques. The fluorescent detection limits on the various aromatic compounds show particularly high sensitivities. For example, the detection limits for most polycyclic aromatic hydrocarbons and the aldehydic and ketonic derivatives range around 10 nanograms. The identification limits of the polycyclic and heterocyclic hydrocarbons range around 1 nanogram; those of the polynuclear aromatic amines range around 10 - 1000 nanograms. Although impressive, even better sensitivities obtain when one uses a laser as an illuminating source and a nondispersive, low f-number spectrometer to collect the scattered light.

In accordance with this invention a laser beam is used to sequentially illuminate airborne particles brought to the analyzing apparatus by an appropriate aerosol-handling system. The light scattered by the illuminated particles contains both unshifted (Rayleigh) and shifted (Raman and fluorescent) components. The Rayleigh component indicates the physical presence and nominal size of the scattering particle; the Raman and fluorescent components measure, in addition, the mass and chemistry of the target particle. The detection and sizing operations are carried out by collecting the Rayleigh-scattered light and measuring its intensity with a photo-multiplier tube. Similarly, the weighing and assaying operations are accomplished by measuring, respectively, the intensity and frequency of the Raman and/or fluorescent-scattered light. (The frequencies observed in the Raman-scattered and fluorescent-scattered light correspond to the chemical components of the particle; the intensity at each frequency is proportional to the mass of that chemical component present in the particle.

BRIEF DESCRIPTION OF THE DRAWINGS

FIG. 1 is a block diagram of an embodiment of the invention.

FIG. 2 is an enlarged sectional schematic view of a scattering chamber and aerosol injection system suitable for use with this invention.

DESCRIPTION OF THE PREFERRED EMBODIMENT

Referring now to FIG. 1, there may be seen a block diagram of an embodiment of this invention. A continuous wave laser system 10, directs a laser beam at the scattering region 12, (the details of which are shown in FIG. 22), where injected aerosol particles scatter Rayleigh, Raman, and fluorescent radiation toward a collecting lens 14. A beam monitor circuit 16 is used to monitor the intensity of the laser beam, generating a signal representative thereof and feeding it back to the CW laser system 10 for the purpose of maintaining the beam intensity constant.

The collecting lens 14 collimates the light and directs it toward a 45° dichroic filter 18. The dichroic filter separates the Rayleigh component from the Raman and fluorescent components by reflecting the Rayleigh components toward a Rayleigh photomultiplier 20. Raman and fluorescent components pass through the dichroic filter and then through a narrow band interference filter 22, onto the Raman-fluorescent photomultiplier 24.

The output of the Rayleigh photomultiplier is applied to a signal amplifier 26, whose output is applied to a pulse shaper 28. The shaped pulses are then applied to an area integrator 30. The area integrator output is applied to a pulse-height analyzer 32, and also to a pulse counter 34. To determine the particle concentration, the pulse counter multiplies the number of pulses counted per second times a geometrical constant. The geometrical constant is determined by the geometry of the aerosol stream, the shape of the laser beam and the cubic feet per unit time of aerosol passing through the chamber, and is the reciprocal of the volume of aerosol passed through the laser beam each second. The count is converted to an analog current by a digital-to-analog converter 35. The result is displayed by a damped ammeter 36 called a "Particle ConcentrationMeter."

Narrow band filter 22 is selected to pass the frequencies of interest when it is desired to measure Raman illumination and is selected to pass the frequencies of interest when it is desired to measure fluorescent illumination. Thus, two narrow band filters 22 are required, one for Raman illumination measurement and the other for fluorescent illumination measurement. The equipment that follows the narrow band filter is the same for both measurements, but measures either Raman or fluorescent radiation, as determined by the bandwidth of filter 22.

The output of the photomultiplier 24, which responds to either Raman or fluorescent radiation, as passed by filter 22, is applied to a signal amplifier 36. The output of the signal amplifier is applied to a pulse shaper 38, and the pulse shaper output is applied to an area integrator 40. The area integrator pulse integrates each pulse and its output is applied to a pulse counter circuit which counts the pulses and multiplies them by a geometric constant. The resulting count is converted to an analog current by a digital-to-analog converter 42, the output of which is applied to a damped ammeter called a "Particle Concentration Meter" 43.

The output of the integrator circuit 40 is also applied to the pulse height-analyzer 32. The pulse height-analyzer output is applied to a teletypewriter 44.

The area integrator 30, effectively measures the area of each electronic pulse which in turn is proportional to the cross-sectional area of the scattering particle. The pulse-height analyzer 32, histograms the integrated pulses thereby producing a Rayleigh size-frequency distribution curve. The pulse-height analyzer is also used to histogram the integrated Raman/fluorescent pulses, thereby producing a mass-frequency distribution curve. When operating in the automated mode, the pulse-height analyzer periodically outputs its distribution curves to the teletypewriter for permanent data recording.

Another purpose of the interference filter 22, to which the Raman and fluorescent scattered light is applied, is to select a given Raman fluorescent line from the several present, thereby making the instrument specific to a given chemical compound. The dichroic-filter-/interference-filter combination provides a Rayleigh rejection ratio better than $10^8$ and a Raman/fluorescent transmission of approximately 50%. The pulse-counter circuit records the number of light pulses received per unit time and displays the result in particles of a specific chemistry per unit of volume with a current meter.

Figure 2:
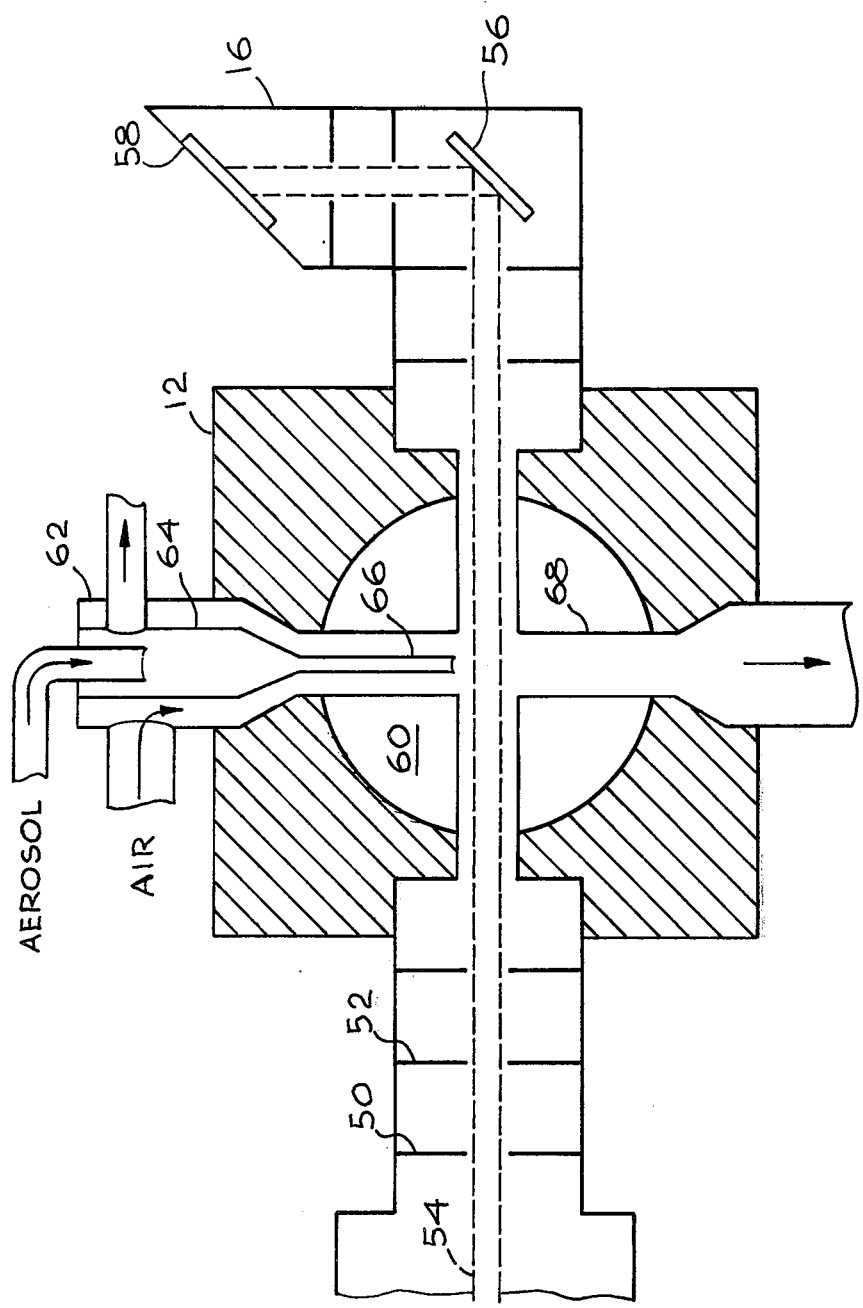

FIG. 2 is an oversized view in cross section of a scattering chamber and aerosol injection system which may be used with the embodiment of the invention. Collimating baffles 50, 52, by way of example, limit the width of the laser beam, here represented by dashed lines 54. The beam passes through the center cavity 60 of the scattering chamber structure 12, strikes a mirror 56 in the beam absorber, which reflects the beam to the photodetector 58 in the beam monitoring circuit 16.

The scattering chamber 12 comprises walls, defining at the center thereof the cavity 60, which comprises the scattering chamber. A constant flow of air is pumped into a tube 62, coaxially within which is a second tube 64, which necks down to a capillary portion 66. The capillary portion terminates just above the region through which the laser beam passes. The walls of the block 12 have openings therein to permit the passage of the laser beam therethrough so that it will pass through the scattering chamber and then strikes the mirror 56. Another tube 68, which is diametrically opposite the tube 62 and the capillary section 68, provides an exit for air and aerosol.

A suitable volume of the aerosol to be analyzed, is applied by suitable pumping means and is introduced into the airstream by means of the capillary section 66. The airstream thus is used to form a protective jacket or sheath around the aerosol stream. The boundary layer so formed also ensures laminar flow, suppresses turbulence, and maintains the aerosol stream width. Additionally, the air sheath prevents aerosol particles from landing on optical components thereby increasing the stray light level. By way of example, the ratio of the air to the injected aerosol may be made on the order of 100:1. The injection capillary may be made on the order of 0.2mm in diameter and 10mm in length. The width (0.2mm) of the aerosol stream is made considerably smaller than the width (approximately 1.5mm) of the laser beam. Accordingly, the intensity profile traversed by an aerosol particle is nearly independent of the point of injection.

As described above, light scattered by an aerosol particle passes via the lens and dichroic filter to the photocathodes of the photomultiplier tubes. The duration of each photomultiplier pulse is determined by the time required for a particle to cross the laser beam. Roughly speaking, the pulse length $\tau$ equals the distance $2r_O$, ($r_O$ = beam radius) travelled divided by the aerosol flow velocity, $V_O$. Within broad limits, the traverse time remains independent of the size and shape of the particle.

The shape of the recorded pulse corresponds to the intensity profile traversed by the aerosol particle. For a radially symmetric, Gaussian-shaped laser beam, the intensity profile also looks Gaussian. Accordingly, particle size can be estimated by examining either the peak pulse amplitude or the total pulse area. The pulse-area technique leads to better signal-to-noise ratios (SNRs) since high frequency noise is averaged away when integrating for the pulse area. (Higher SNR provides, of course, more sensitivity to small particles.)

The electronic circuits shown and described in connection with FIG. 1 are standard, well-known, and commercially available circuits. The area integrator circuit for example may constitute a differential amplifier having a capactive-feedback configuration wherein each pulse is integrated. Following the integration the capacitor is discharged and a signal having a fixed width but with an amplitude equal to the voltage on the capacitor is obtained.

The particle concentration display circuits count the pulses generated by particles with diameters above a specific but variable size. The count is converted into an analog current which may be considered as proportional to the concentration of particulate matter. This is passed through a damped ammeter whereby the concentration of particulate matter may be continuously displayed. With knowledge of the aerosol flow rate into the scattering chamber and of the particle count per unit of time, the number of particles per unit volume can be determined.

The pulse-height analyzer sorts signals received from the area integrator according to amplitude and then displays the signals as a histogram on an oscilloscope screen. By way of example, but not to be considered as a limitation upon the invention, a suitable pulse analyzer is a commercial device made by Northern Scientific Co. (Model 602) which allows automated operation of the laser Raman/fluorescent particle counter. In particular, this device contains an internal clock that periodically directs the analyzer to output its accumulated histogram to the teletypewriter 44. After printing the histogram, the analyzer begins forming a new histogram.

The nominal or equivalent diameter of the various particles is determined by measuring the height or area of the electronic pulses caused by the aerosol particles. Roughly speaking, the pulse height and area increase as the square of the particle's root-mean-square diameter.

The mass of the various particles is determined by measuring the intensity of the Raman-shifted spectral lines. The intensity of these line varies directly with the number of molecules in a particle, assuming that the particle is chemically pure. The histogram provides the intensity measurement from which mass is determined.

As previously pointed out, upon proper excitation of a particle it will fluoresce at a particular wavelength or wavelengths depending on the particle composition and the exciting frequency. Curves are available which indicate the fluorescent intensity as a function of the emission wavelength for a particular exciting frequency. Thus, by the selection of an appropriate central frequency and a moderate spectral bandwidth, one can detect the presence of a particular spectral line indicative of the presence of a particular chemical.

There has accordingly been described and shown herein a novel and useful optical device for counting, sizing, weighing and assaying airborne particles.

I claim:

1. Apparatus for determining the physical and chemical state of aerosol particles comprising
    laser means for establishing a light beam,
    means for passing a stream of aerosol particles through said light beam whereby each said particle generates Raman and fluorescent radiation in addition to Rayleigh radiation
    dichroic filter means for separating said Raman and fluorescent radiations from said Rayleigh radiation,
    bandpass filter means in the path of said Raman and fluorescent radiations for passing a selected portion of either the Raman or fluorescent radiation therethrough having frequencies in accordance with the chemical composition of the particles whose physical and chemical states it is desired to be determined.
    photomultiplier means for generating pulse signals responsive to the radiation from each particle that has passed through said bandpass filter means,
    means to which the output of said photomultiplier means is applied for producing a display of particles in the stream passing through said laser beam sorted in accordance with the size of the masses,
    means to which the output of said photomultiplier means is also applied to producing a display indicative of the mass concentration of particles in the stream passing through said laser beam,
    Rayleigh photomultiplier means for generating a pulse signal responsive to the Rayleigh radiation from each particle, and
    means responsive to a plurality of said pulse signals for providing a display representative of the particle size distribution for a given volume of said aerosol particle stream.

2. Apparatus for determining the physical and chemical state of aerosol particles in a stream comprising
    laser means for establishing a light beam,
    means for passing a stream of aerosol particles through said light beam whereby each said particle generates Raman and fluorescent radiation in addition to Rayleigh radiation,
    dichroic filter means for separating said Raman and fluorescent radiation from said Rayleigh radiation,
    interference filter means in the path of said Raman and fluorescent radiation for enabling Raman or fluorescent radiation having a predetermined frequency to pass through, said predetermined frequency being a function of the chemical composition of the particle,
    photomultiplier means for generating a pulse signal responsive to the Raman or fluorescent radiation from each particle that has passed through said interference filter means,
    means for integrating each pulse signal generated by said photomultiplier means to provide pulses each having an amplitude representative of the mass of a particle,
    means to which the output of said means for integrating is applied for sorting said pulses in accordance with amplitude and displaying said amplitude sorted pulses as a histogram,
    means to which the output of said means for integrating is applied for counting pulses having an amplitude in excess of a predetermined level occurring over a predetermined interval,
    means for coverting the number of pulses counted by said means for counting pulses having an amplitude in excess of a predetermined level to an analog signal representative thereof,
    means for displaying said analog signal indicative of the mass concentration of said particle,
    Rayleigh photomultiplier means for generating a pulse signal responsive to the Rayleigh radiation from each particle, and
    means to which the output of said Rayleigh photomultiplier means is applied for providing a display representative of the particle size distribution for a given volume of said aerosol particle stream.

3. The method of determining physical and chemical properties of aerosol particles comprising
    establishing a high intensity light beam of a predetermined diameter,
    passing a stream of said aerosol particles across said light beam to produce Rayleigh, Raman and fluorescent radiations for each particle,
    separating said Raman and fluorescent radiations from said Rayleigh radiation,
    choosing a selected portion of either the Raman or fluorescent radiation from the remainder of said Raman and fluorescent radiations which has been separated from the Rayleigh radiation, said selected portion having frequencies indicative of the presence of predetermined chemicals in said particles,
    generating a first pulse signal from the portion of of the selected radiation of each particle,
    producing a first display from said generated first pulse signals which is representative of the mass concentration of aerosol particles in the stream passing through said light beam,
    producing a second display from said first generated pulse signals which indicates aerosol particles in accordance with the size of their masses,
    generating a second signal from the Rayleigh radiation of each particle; and
    producing a third display from said second generated pulse signals responsive to Rayleigh radiations, representative of particle size distribution for a given aerosol particle stream volume.

4. The method as recited in claim 3 wherein each of the steps of generating a first pulse signal and a second pulse signal, includes
    integrating each of said first and second pulse signals to produce integrated first and second pulse signals, respectively.

5. The method as recited in claim 4 wherein said step of producing the first display includes
    counting the number of said first integrated pulse signals over a predetermined amplitude occurring within a predetermined interval to obtain a pulse count,
    converting said pulse count to an analog signal, and
    displaying said analog signal 6. The method as recited in claim 4 wherein said step of producing the second display representative of the size of the masses of said particles includes
   means for sorting said first integrated pulse signals in accordance with their sizes.

7. A method of determining properties of aerosol particles, the steps comprising:
   establishing a high intensity light beam of a predetermined diameter;
   passing said light beam through a stream consisting of a stream of aerosol particles surrounded by a stream of air to produce Rayleigh, Raman and fluorescent radiation from the aerosol particles;
   separating the Rayleigh radiation from the Raman and fluorescent radiations;
   selecting a portion of either the Raman or the fluorescent radiation;
   utilizing the Rayleigh radiation to provide data related to the sizes of the aerosol particles; and
   utilizing the selected radiation portion to provide data related to the masses of the aerosol particles.

* * * * *